United States Patent
Guthart et al.

(10) Patent No.: US 8,944,070 B2
(45) Date of Patent: Feb. 3, 2015

(54) NON-FORCE REFLECTING METHOD FOR PROVIDING TOOL FORCE INFORMATION TO A USER OF A TELESURGICAL SYSTEM

(75) Inventors: Gary S. Guthart, Mountain View, CA (US); David Q. Larkin, Menlo Park, CA (US); David J. Rosa, San Jose, CA (US); Paul W. Mohr, Mountain View, CA (US); Giuseppe Prisco, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1603 days.

(21) Appl. No.: 11/093,372

(22) Filed: Mar. 30, 2005

(65) Prior Publication Data

US 2005/0200324 A1    Sep. 15, 2005

Related U.S. Application Data

(63) Continuation-in-part of application No. 10/314,001, filed on Dec. 5, 2002, now Pat. No. 7,107,090, which is a continuation of application No. 09/464,455, filed on Dec. 14, 1999, now Pat. No. 6,522,906, which is a (Continued)

(51) Int. Cl.
*A61B 19/00*    (2006.01)
*A61B 1/04*     (2006.01)
(Continued)

(52) U.S. Cl.
CPC ....... *A61B 19/5244* (2013.01); *A61B 2019/507* (2013.01); *A61B 19/22* (2013.01); *A61B 19/2203* (2013.01); *A61B 19/52* (2013.01); *A61B 19/5212* (2013.01); *A61B 2019/2223* (2013.01); *A61B 2019/223* (2013.01); *A61B 2019/2234* (2013.01); *A61B 2019/265* (2013.01); *A61B 1/0005* (2013.01); *A61B 1/04* (2013.01);

(Continued)

(58) Field of Classification Search
USPC ............................ 606/1; 700/245; 901/2; 3/1
See application file for complete search history.

(56) References Cited

U.S. PATENT DOCUMENTS

| 3,628,535 | A | 12/1971 | Ostrowsky et al. |
| 3,818,284 | A | 6/1974 | DeVersterre et al. |

(Continued)

FOREIGN PATENT DOCUMENTS

| EP | 812662 A1 | 12/1997 |
| EP | 1125557 A2 | 8/2001 |

(Continued)

OTHER PUBLICATIONS

M. Tavakoli, A Force Refelective Master Slave System for Minimally Invasive Surgery Proceeding of the 2003 IEER/RSJ Intl Conf. on Intelligent Robots & System, Oct. 2003 , p. 3077.

(Continued)

*Primary Examiner* — Aaron Roane (57) ABSTRACT

Tool force information is provided to a user of a telesurgical system using an alternative modality other than force reflection on a master manipulator, such as providing the information on user-visible, user-audible, or haptic "buzz" or "viscosity" indicators, so as to allow expanded processing, including amplification, of the information, while not significantly affecting the stability of the telesurgical system or any closed-loop control systems in the telesurgical system.

22 Claims, 9 Drawing Sheets

Related U.S. Application Data continuation-in-part of application No. 09/457,406, filed on Dec. 7, 1999, now Pat. No. 6,799,065, application No. 11/093,372, which is a continuation-in-part of application No. 10/644,406, filed on Aug. 19, 2003, now abandoned, which is a continuation of application No. 10/163,626, filed on Jun. 5, 2002, now Pat. No. 6,671,581, which is a continuation of application No. 09/373,678, filed on Aug. 13, 1999, now Pat. No. 6,424,885.

(60) Provisional application No. 60/128,160, filed on Apr. 7, 1999.

(51) Int. Cl.
*A61B 8/12* (2006.01)
*A61B 17/00* (2006.01)
*A61B 1/00* (2006.01)
*A61B 1/313* (2006.01)

(52) U.S. Cl.
CPC ............. *A61B1/3132* (2013.01); *A61B 8/12* (2013.01); *A61B 17/00234* (2013.01)
USPC ........ 128/898; 606/1; 606/4; 606/19; 606/54; 606/58

(56) References Cited

U.S. PATENT DOCUMENTS

| | | |
|---|---|---|
| 3,905,215 A | 9/1975 | Wright |
| 3,923,166 A | 12/1975 | Fletcher et al. |
| 4,150,326 A | 4/1979 | Engelberger et al. |
| 4,349,837 A | 9/1982 | Hinds |
| 4,588,348 A * | 5/1986 | Beni et al. ................ 414/730 |
| 4,644,237 A | 2/1987 | Frushour et al. |
| 4,672,963 A | 6/1987 | Barken |
| 4,722,056 A | 1/1988 | Roberts et al. |
| 4,762,455 A | 8/1988 | Coughlan et al. |
| 4,762,456 A | 8/1988 | Nelson |
| 4,791,934 A | 12/1988 | Brunnett |
| 4,831,549 A | 5/1989 | Red et al. |
| 4,833,383 A | 5/1989 | Skarr et al. |
| 4,837,703 A | 6/1989 | Kakazu et al. |
| 4,837,734 A | 6/1989 | Ichikawa et al. |
| 4,839,838 A | 6/1989 | LaBiche et al. |
| 4,853,874 A | 8/1989 | Iwamoto et al. |
| 4,858,149 A | 8/1989 | Quarendon |
| 4,860,215 A | 8/1989 | Seraji |
| 4,863,133 A | 9/1989 | Bonnell |
| 4,942,539 A | 7/1990 | McGee et al. |
| 4,979,949 A | 12/1990 | Matsen, III |
| 4,984,157 A | 1/1991 | Cline et al. |
| 4,989,253 A | 1/1991 | Liang et al. |
| 5,046,022 A | 9/1991 | Conway et al. |
| 5,053,976 A | 10/1991 | Nose et al. |
| 5,079,699 A | 1/1992 | Tuy et al. |
| 5,086,401 A | 2/1992 | Glassman et al. |
| 5,098,426 A | 3/1992 | Sklar et al. |
| 5,099,846 A | 3/1992 | Hardy |
| 5,142,930 A | 9/1992 | Allen et al. |
| 5,170,347 A | 12/1992 | Tuy et al. |
| 5,182,641 A | 1/1993 | Diner et al. |
| 5,184,009 A * | 2/1993 | Wright et al. ............ 250/227.11 |
| 5,184,601 A | 2/1993 | Putman |
| 5,187,796 A | 2/1993 | Wang et al. |
| 5,217,003 A | 6/1993 | Wilk |
| 5,230,338 A | 7/1993 | Allen et al. |
| 5,230,623 A | 7/1993 | Guthrie et al. |
| 5,235,510 A | 8/1993 | Yamada et al. |
| 5,239,246 A * | 8/1993 | Kim ........................ 318/568.11 |
| 5,251,127 A | 10/1993 | Raab |
| 5,257,203 A | 10/1993 | Riley et al. |
| 5,261,404 A | 11/1993 | Mick et al. |
| 5,266,875 A | 11/1993 | Slotine |
| 5,279,309 A | 1/1994 | Taylor et al. |
| 5,299,288 A | 3/1994 | Glassman et al. |
| 5,313,306 A | 5/1994 | Kuban et al. |
| 5,321,353 A | 6/1994 | Furness |
| 5,341,950 A | 8/1994 | Sinz |
| 5,343,385 A | 8/1994 | Joskowicz et al. |
| 5,368,015 A | 11/1994 | Wilk |
| 5,368,428 A | 11/1994 | Hussey et al. |
| 5,382,885 A | 1/1995 | Salcudean et al. |
| 5,397,323 A | 3/1995 | Taylor et al. |
| 5,402,801 A | 4/1995 | Taylor |
| 5,408,409 A | 4/1995 | Glassman et al. |
| 5,417,210 A | 5/1995 | Funda et al. |
| 5,430,643 A | 7/1995 | Seraji |
| 5,445,166 A | 8/1995 | Taylor |
| 5,454,827 A | 10/1995 | Aust et al. |
| 5,474,571 A | 12/1995 | Lang |
| 5,503,320 A | 4/1996 | Webster et al. |
| 5,515,478 A | 5/1996 | Wang |
| 5,524,180 A | 6/1996 | Wang et al. |
| 5,528,955 A | 6/1996 | Hannaford et al. |
| 5,531,742 A | 7/1996 | Barken |
| 5,553,198 A | 9/1996 | Wang et al. |
| 5,617,858 A | 4/1997 | Taverna et al. |
| 5,624,398 A | 4/1997 | Smith et al. |
| 5,631,973 A | 5/1997 | Green |
| 5,638,819 A | 6/1997 | Manwaring et al. |
| 5,657,429 A | 8/1997 | Wang et al. |
| 5,695,500 A * | 12/1997 | Taylor et al. .................. 606/130 |
| 5,704,897 A | 1/1998 | Truppe |
| 5,715,729 A | 2/1998 | Toyama et al. |
| 5,737,500 A | 4/1998 | Seraji et al. |
| 5,748,767 A | 5/1998 | Raab |
| 5,754,741 A | 5/1998 | Wang et al. |
| 5,755,725 A | 5/1998 | Druais |
| 5,762,458 A | 6/1998 | Wang et al. |
| 5,784,542 A | 7/1998 | Ohm et al. |
| 5,791,231 A | 8/1998 | Cohn et al. |
| 5,792,135 A | 8/1998 | Madhani et al. |
| 5,797,900 A | 8/1998 | Madhani |
| 5,807,377 A | 9/1998 | Madhani |
| 5,808,665 A | 9/1998 | Green |
| 5,810,880 A | 9/1998 | Jensen et al. |
| 5,814,038 A | 9/1998 | Jensen et al. |
| 5,815,640 A | 9/1998 | Wang et al. |
| 5,820,545 A | 10/1998 | Arbter et al. |
| 5,820,623 A | 10/1998 | Ng |
| 5,841,950 A | 11/1998 | Wang et al. |
| 5,855,553 A | 1/1999 | Tajima et al. |
| 5,855,583 A | 1/1999 | Wang et al. |
| 5,859,934 A | 1/1999 | Green |
| 5,876,325 A | 3/1999 | Mizuno et al. |
| 5,877,819 A | 3/1999 | Branson |
| 5,878,193 A | 3/1999 | Wang et al. |
| 5,907,664 A | 5/1999 | Wang et al. |
| 5,911,036 A | 6/1999 | Wright et al. |
| 5,931,832 A | 8/1999 | Jensen |
| 5,938,678 A | 8/1999 | Zirps et al. |
| 5,950,629 A | 9/1999 | Taylor et al. |
| 5,964,707 A | 10/1999 | Fenster et al. |
| 5,971,976 A | 10/1999 | Wang et al. |
| 5,980,460 A | 11/1999 | Oestensen et al. |
| 5,980,461 A | 11/1999 | Rajan |
| 5,987,591 A | 11/1999 | Jyumonji |
| 5,993,390 A | 11/1999 | Savord et al. |
| 5,993,391 A | 11/1999 | Kamiyama |
| 6,019,724 A | 2/2000 | Gronningsaeter et al. |
| 6,063,095 A | 5/2000 | Wang et al. |
| 6,084,371 A | 7/2000 | Kress |
| 6,096,025 A | 8/2000 | Borders |
| 6,120,433 A | 9/2000 | Mizuno et al. |
| 6,196,081 B1 | 3/2001 | Yau |
| 6,224,542 B1 | 5/2001 | Chang et al. |
| 6,246,200 B1 | 6/2001 | Blumenkranz et al. |
| 6,270,453 B1 | 8/2001 | Sakai |
| 6,292,712 B1 | 9/2001 | Bullen |
| 6,307,285 B1 | 10/2001 | Delson et al. |
| 6,312,435 B1 | 11/2001 | Wallace et al. |
| 6,325,808 B1 | 12/2001 | Bernard et al. |

(56) References Cited

U.S. PATENT DOCUMENTS

| | | | |
|---|---|---|---|
| 6,330,837 B1 | 12/2001 | Charles et al. | |
| 6,331,181 B1 | 12/2001 | Tierney et al. | |
| 6,371,952 B1 | 4/2002 | Madhani | |
| 6,394,998 B1 | 5/2002 | Wallace et al. | |
| 6,398,726 B1 | 6/2002 | Ramans et al. | |
| 6,424,885 B1 * | 7/2002 | Niemeyer et al. | 700/245 |
| 6,425,865 B1 | 7/2002 | Salcudean et al. | |
| 6,442,417 B1 | 8/2002 | Shahidi et al. | |
| 6,459,926 B1 | 10/2002 | Nowlin | |
| 6,468,265 B1 | 10/2002 | Evans et al. | |
| 6,493,608 B1 | 12/2002 | Niemeyer | |
| 6,522,906 B1 | 2/2003 | Salisbury, Jr. et al. | |
| 6,569,084 B1 | 5/2003 | Mizuno et al. | |
| 6,574,355 B2 | 6/2003 | Green | |
| 6,594,552 B1 | 7/2003 | Nowlin | |
| 6,645,196 B1 | 11/2003 | Nixon | |
| 6,659,939 B2 | 12/2003 | Moll | |
| 6,671,581 B2 | 12/2003 | Niemeyer et al. | |
| 6,676,669 B2 * | 1/2004 | Charles et al. | 606/130 |
| 6,699,177 B1 | 3/2004 | Wang | |
| 6,770,081 B1 | 8/2004 | Cooper et al. | |
| 6,786,896 B1 * | 9/2004 | Madhani et al. | 606/1 |
| 6,799,065 B1 | 9/2004 | Niemeyer | |
| 6,837,883 B2 | 1/2005 | Moll et al. | |
| 6,847,922 B1 | 1/2005 | Wampler, II | |
| 6,926,709 B2 | 8/2005 | Bieger et al. | |
| 6,991,627 B2 | 1/2006 | Madhani et al. | |
| 7,107,090 B2 | 9/2006 | Salisbury et al. | |
| 7,155,315 B2 | 12/2006 | Niemeyer et al. | |
| 7,181,315 B2 | 2/2007 | Watanabe et al. | |
| 7,194,118 B1 | 3/2007 | Harris et al. | |
| 7,491,198 B2 | 2/2009 | Kockro | |
| 7,574,250 B2 | 8/2009 | Niemeyer | |
| 7,806,891 B2 | 10/2010 | Nowlin et al. | |
| 7,819,859 B2 | 10/2010 | Prisco et al. | |
| 7,963,913 B2 | 6/2011 | Devengenzo et al. | |
| 7,979,157 B2 | 7/2011 | Anvari | |
| 8,062,288 B2 | 11/2011 | Cooper et al. | |
| 8,120,301 B2 | 2/2012 | Goldberg et al. | |
| 8,130,907 B2 | 3/2012 | Maurer, Jr. et al. | |
| 8,155,479 B2 | 4/2012 | Hoffman et al. | |
| 8,170,716 B2 | 5/2012 | Coste-Maniere et al. | |
| 8,221,304 B2 | 7/2012 | Shioda et al. | |
| 8,256,319 B2 | 9/2012 | Cooper et al. | |
| 8,315,720 B2 | 11/2012 | Mohr et al. | |
| 8,335,590 B2 | 12/2012 | Costa et al. | |
| 2001/0035871 A1 | 11/2001 | Bieger et al. | |
| 2002/0045905 A1 | 4/2002 | Gerbi et al. | |
| 2002/0120188 A1 | 8/2002 | Brock et al. | |
| 2003/0032878 A1 | 2/2003 | Shahidi | |
| 2003/0055410 A1 | 3/2003 | Evans et al. | |
| 2003/0109780 A1 | 6/2003 | Coste-Maniere et al. | |
| 2004/0039485 A1 | 2/2004 | Niemeyer et al. | |
| 2004/0106916 A1 | 6/2004 | Quaid et al. | |
| 2004/0238732 A1 | 12/2004 | State et al. | |
| 2005/0054895 A1 | 3/2005 | Hoeg et al. | |
| 2005/0059960 A1 | 3/2005 | Simaan et al. | |
| 2005/0096502 A1 | 5/2005 | Khalili | |
| 2005/0203380 A1 | 9/2005 | Sauer et al. | |
| 2005/0251113 A1 | 11/2005 | Kienzle, III | |
| 2006/0142657 A1 | 6/2006 | Quaid et al. | |
| 2006/0258938 A1 | 11/2006 | Hoffman et al. | |
| 2006/0261770 A1 | 11/2006 | Kishi et al. | |
| 2007/0013336 A1 | 1/2007 | Nowlin et al. | |
| 2007/0038080 A1 | 2/2007 | Salisbury, Jr. et al. | |
| 2007/0135803 A1 | 6/2007 | Belson | |
| 2007/0142968 A1 | 6/2007 | Prisco et al. | |
| 2007/0265491 A1 | 11/2007 | Krag et al. | |
| 2007/0270650 A1 | 11/2007 | Eno et al. | |
| 2007/0283970 A1 | 12/2007 | Mohr et al. | |
| 2007/0287884 A1 | 12/2007 | Schena | |
| 2007/0287992 A1 | 12/2007 | Diolaiti et al. | |
| 2008/0004603 A1 | 1/2008 | Larkin et al. | |
| 2008/0033240 A1 | 2/2008 | Hoffman et al. | |
| 2008/0065105 A1 | 3/2008 | Larkin et al. | |
| 2008/0065109 A1 | 3/2008 | Larkin | |
| 2008/0081992 A1 | 4/2008 | Kagermeier | |
| 2008/0118115 A1 | 5/2008 | Williamson | |
| 2008/0140087 A1 | 6/2008 | Barbagli | |
| 2008/0247506 A1 | 10/2008 | Maschke | |
| 2009/0012531 A1 | 1/2009 | Quaid et al. | |
| 2009/0036902 A1 | 2/2009 | DiMaio et al. | |
| 2009/0088634 A1 | 4/2009 | Zhao et al. | |
| 2009/0192524 A1 | 7/2009 | Itkowitz et al. | |
| 2009/0248036 A1 | 10/2009 | Hoffman et al. | |
| 2009/0326553 A1 | 12/2009 | Mustufa et al. | |
| 2011/0105898 A1 | 5/2011 | Guthart et al. | |
| 2014/0051922 A1 | 2/2014 | Guthart et al. | |

FOREIGN PATENT DOCUMENTS

| | | |
|---|---|---|
| WO | WO-9501757 | 1/1995 |
| WO | WO-9729690 | 8/1997 |
| WO | WO-9743942 A1 | 11/1997 |
| WO | WO-9743943 A1 | 11/1997 |
| WO | WO-2004014244 | 2/2004 |
| WO | WO-2006079108 A1 | 7/2006 |
| WO | WO-2007088208 A1 | 8/2007 |
| WO | WO-2007136768 A2 | 11/2007 |
| WO | WO-2007146987 A2 | 12/2007 |
| WO | WO-2008002830 A2 | 1/2008 |
| WO | WO-2008103383 A1 | 8/2008 |
| WO | WO-2009034477 | 3/2009 |
| WO | WO-2009037576 | 3/2009 |
| WO | WO-2009158164 A1 | 12/2009 |
| WO | WO-2010039394 A1 | 4/2010 |

OTHER PUBLICATIONS

Kitagawa, Masaya, Effects of Sensory Substituion on Suture Manipulation Forces for Surgical Teleoperation, Journal of Thoracic and Cardiovascular Surgery.2005; 129: 151-158.

Vertut, Jean and Coeffet, Philippe Coiffet; "Robot Technology; vol. 3A Teleoperation and Robotics Evolution and Development"; 1986; Prentice-Hall, Inc; Englewood Cliffs, N.J.

Adams et al. "Computer-assisted surgery" IEEE Computer Graphics and Applications, pp. 43-51 (1990).

Askew et al. "Ground control testbed for space station freedom robot manipulators," IEEE Virtual Reality Annual International Symposium, Sep. 18-22, 1993, Seattle, Washington, pp. 60-75 (1993).

Bjura et al., "Merging virtual objects with the real world: Seeing ultrasound imagery within the patient" Computer Graphics 26(2):203-210(1992).

Cao et al. "Task and motion analysis in endoscopic surgery" Submitted for Fifth Annual Symposium on Haptic Interfaces for Virtual; Environment and Teleoperator Systems for the Winter Meeting of ASME, pp. 1-32 (1998).

Christensen et al. "Model based, sensor directed remediation of underground storage tanks," Proceedings of the IEEE International Conference on Robotics and Automation (1991) pp. 1377-1383.

Dolan et al., "A robot in an operating room; A bull in a China shop?" IEEE/Ninth Annual Conference of the Engineering in Medicine and Biology Society (1987).

Elder et al. "Specifying user interfaces for safety-critical medical systems," Second Annual International Symposium on Medical Robotics and Computer Assisted Surgery, pp. 148-165 (1995).

Gayed et al. "An advanced control micromanpulator for surgical applications," Systems Science 13:123-133 (1997).

Harris et al. "A robotic procedure for transurethral resection of the prostate," Second Annual International Symposium on Medical Robotics and Computer Assisted Surgery, pp. 254-271 (1995).

Hunter et al. "A teleoperated microsurgical robot and associated virtual environment for eye surgery," Presence Teleoperators and Virtual Environments, MIT Press 2(4):264-280 (1993).

Hunter et al. "Ophthalmic microsurgical robot and associated virtual environment" Comput. Biol. Med. 25(2):173-183 (1995).

Hurteali et al. "Laparoscopic surgery assisted by a robotic cameraman: Concept and Experimental results," IEEE International Conference on Robotics and Automation, pp. 2288-2289 (1994).

(56) References Cited

OTHER PUBLICATIONS

Jackson et al. "Force feedback and medical simulation," Interactive Technology and the New Paradigm, pp. 147-151 (1995).
Kazerooni "Design and analysis of the statically balanced direct-drive robot manipulator," Robotics and Computer-Integrated Manufacturing 6(4):267-293 (1989).
Kilmer et al. "Watchdog safety computer design and Implementation," RVSME Robots & Conference, pp. 101-117 (1984).
Kosugi et al. "An articulated neurosurgical navigation system using MRI and CT Images," IEEE Transactions on Biomedical Engineering, 35(2):147-152 (1988).
Ng et al., "Robotic surgery" IEEE Engineering in Medicine and Biology, pp. 120-125 (1993).
Paul et al. "Development of a surgical robot for cementless total hip arthroplasty," Clinical Orthopaedics and Related Research 285:57-68 (1992).
Preising et al., "A Literature Review: Robots in Medicine," IEEE Engineering in Medicine and Biology, pp. 13-22 (1991).
Rosenberg "Human Interface hardware for virtual laparoscopic surgery," *Interactive Technology and the New Paradigm for Healthcare*, Morgan et al., Eds., pp. 322-325 (1995).
Schenker et al. "Development of a telemanipulator for dexterity enhanced microsurgery," Second Annual International Symposium on Medical Robotics and Computer Assisted Surgery, pp. 81-88 (1995).
Taylor et al. "A telerobotic assistant for laparoscopic surgery," IEEE Engineering in Medicine and Biology, pp. 279-288 (1995).
Taylor et al. "Research report: A telerobotic assistant for laparoscopic surgery," Computer Science, pp. 1-21 (1994).
Toon "Eye surgery simulator could help physicians learn and practice new techniques," Research Horizons, pp. 22-23 (1993).
Trivedi et al. "Developing telerobotic systems using virtual reality concepts," Proceedings of the 1993 IEEE/RSJ International Conference on Intelligent Robots and Systems(1993).
Debus, et al., "Multichannel vibrotactile display for sensory substitution during teleoperation," Telemanipulator and Telepresence Technologies VIII Conference, Proceeding of SPIE vol. 4570, Newton, MA Oct. 28, 2001.
Alexander, Arthur D. III, "Impacts of Telemation on Modern Society," Symposium on Theory and Practice of Robots and Manipulators, Centre for Mechanical Sciences 1st CISM IFToMM Symposium, Sep. 5-8, 1974, pp. 121-136, vol. 2, Springer-Verlag.
Arai, Tatsuo et al., "Bilateral control for manipulators with different configurations," IECON Inn Conference on Industrial Electronics Control and Instrumentation, Oct. 22-26, 1984, pp. 40-45, vol. 1.
Baumann, Roger, "Haptic Interface for Virtual Reality Based Laparoscopic Surgery Training Environment," Theses No. 1734 Ecole Pholytechnique Federale de Lausanne, 1997, 104 Total Pages.
Bejczy, Antal K. et al., "Controlling Remote Manipulators through Kinesthetic Coupling," Computers in Mechanical Engineering, 1983, pp. 48-60, vol. 1—Issue 1.
Borovoi, A.V., "Stability of a manipulator with force feedback," Izv. AN SSSR Mekhanika Tverdogo Teal, 1990, pp. 37-45, vol. 25—Issue 1, Allerton Press, Inc.
Burdea, Grigore et al., "Dextrous Telerobotics with Force Feedback—an overview. Part 2: Control and Implementation," Robotica, 1991, pp. 291-298, vol. 9.
Christoforou, E.G. et al., "Robotic Arm for Magnetic Resonance Imaging Guided Interventions," 1st IEEE/RAS-EMBS International Conference on Biomedical Robotics and Biomechatronics, Feb. 20-22, 2006, pp. 911-916.
Cohn, Michael C., "Medical Robotics," http://www-bsac.eecs.berkeley.edu/ , 1996, pp. 1-8 and 4.
Colgate, Edward, J., "Power and Impedance Scaling in Bilateral Manipulation," IEEE International Conference on Robotics and Automation, Sacramento, California, Apr. 1991, pp. 2292-2297, vol. 3, IEEE.
Fisher, Scott S., "Virtual interface environment," IEEE/A1AA 7th Digital Avionics Systems Conference Ft. Worth Texas, 1986, pp. 346-350, IEEE.

Fu, K.S. et al., "Robotics: control, sensing, vision, and intelligence," 1987, pp. 12-76 and 201-265, Ch. 2 & 5, McGraw-Hill Book Company.
Fukuda, Toshio et al., "A new method of master-slave type of teleoperation for a micro-manipulator system," IEEE Microrobots and Teleoperations Workshop, 1987, 5 pages, IEEE.
Funda, Janez et al., "Constrained Cartesian Motion Control for Teleoperated Surgical Robots," IEEE Transactions on Robotics and Automation, IEEE, Jun. 1996, vol. 12, No. 3, pp. 453-465.
Furuta, Katsuhisa et al., "Master slave manipulator based on virtual internal model following control concept," IEEE Intl. Conference on Robotics and Automation, 1987, pp. 567-572, vol. 1, IEEE.
Green, Philip, S. et al., "Mobile telepresence surgery," 2nd Annual Intl Symposium on Med. Robotics and Computer Assisted Surgery, Maryland Nov. 1995, pp. 97-103.
Hannaford, Blake et al., "Experimental and simulation studies of hard contact in force reflecting teleoperation," IEEE International Conference on Robotics and Automation Proceedings, 1988, pp. 584-589, vol. 1, IEEE.
Hill, John W., "Telepresence surgery demonstration system," Robotics and Automation, 1994, pp. 2302-2307, vol. 3, SRI International.
Inoue, Masao; "Six-Axis bilateral control of an articulated slave manipulator using a Cartesian master manipulator," Advanced robotics, 1990, pp. 139-150, vol. 4—Issue 2, Robotic society of Japan.
International Preliminary Examination Report for Application No. PCT/US00/08526, mailed on Jun. 29, 2001, 4 pages.
International Search Report for application No. PCT/US00/08526, Mailed on Jul. 14, 2000, 2 pages.
International Search Report for application No. PCT/US99/29145, Mailed on May 15, 2000, 1 page.
Jones, Daniel B. et al., "Next generation 3D videosystems may improve laprascopic task performance," Interactive Technology and the New Paradigm for Healthcare, 1995, pp. 152-160, Ch 25.
Kazerooni, H. et al., "The Dynamics and Control of a Haptic Interface Device," IEEE Transactions on Robotics and Automation, 1994, pp. 453-464, vol. 10—Issue 4, IEEE.
Kazerooni, H., "Human/Robot Interaction via the Transfer of Power and Information Signals Part I: Dynamics and Control Analysis," IEEE International Conference on Robotics and Automation, 1989, pp. 1632-1640, IEEE.
Kim, Won S. et al., "Active compliance and damping in telemanipulator control," Jet Propulsion Laboratory New technology Report, 1991, pp. 1-14a, vol. 15—Issue 4, JPL & NASA Case No. NP0-1796917466, Item 40.
Komada, Satoshi et al., "Bilateral robot hand based on estimated force feedback," IEEE Proceedings IECON 87 Cambridge MA, Nov. 3-6, 1987, pp. 602-607, vol. 2, IEEE.
Kwoh, Yik, San et al., "A Robot With Improved Absolute Positioning Accuracy for CT Guided Stereotactic Brain Surgery," IEEE Transactions on Biomedical Engineering, Feb. 1988, pp. 153-160, vol. 35—Issue 2, IEEE.
Lazarevic, Zoran, "Feasibility of a Stewart Platform with Fixed Actuators as a Platform for CABG Surgery Device," 1997, 45 pages, Master's Thesis Columbia University Department of Bioengineering.
Madhani, Akhil J., "Design of Teleoperated Surgical Instruments for Minimally Invasive Surgery," Feb. 1998, pp. 1-251.
Massie, Thomas H. et al., "The PHANTOM Haptic Interface: A Device for Probing Virtual Objects," Proceedings of the ASME Winter Annual Meeting, Symposium on Haptic Interfaces for Virtual Environment and Teleoperator Systems, 1994, 7 pages.
Mitsuishi, Mamoru et al., "A tele-micro-surgery system with co-located view and operation points and a rotational-force-feedback-free master manipulator," 2nd Annual Intl. Symposium on Medical robotics and Computer Assisted Surgery Baltimore Maryland, Nov. 4-7, 1995, pp. 111-118.
Neisius B. et al., "Robotic manipulator for endoscopic handling of surgical effectors and cameras," 1st Intl. Symposium on Medical Robotics and Computer Assisted Surgery, 1994, pp. 169-176, vol. 2.
PCT/US07/71850 International Search Report and Written Opinion of the International Searching Authority, mailed Feb. 13, 2009, 9 pages.

(56) References Cited

OTHER PUBLICATIONS

PCT/US09/46234 International Search Report and Written Opinion of the International Searching Authority, mailed Sep. 9, 2009, 13 pages.
PCT/US09/56078 International Search Report and Written Opinion of the International Searching Authority, mailed Jan. 20, 2010, 12 pages.
PCT/US10/28886 International Search Report and Written Opinion of the International Searching Authority, mailed Jul. 6, 2010, 11 pages.
PCT/US10/28897 International Search Report and Written Opinion of the International Searching Authority, mailed Jul. 19, 2010, 16 pages.
PCT/US10/38246 International Search Report and Written Opinion of the International Searching Authority, mailed Sep. 14, 2010, 17 pages.
PCT/US2011/036109 International Search Report and Written Opinion of the International Searching Authority, mailed Oct. 19, 2011, 16 pages.
PCT/US2011/036109 Invitation to Pay Additional Fees and Partial International Search Report, mailed Aug. 18, 2011, 5 pages.
Sastry, Shankar et al., "Millirobotics for remote minamally invasive surgery," Proceedings of the Intl. Workshop on Some Critical Issues in Robotics, Singapore, Oct. 2-3, 1995, pp. 81-98.
Sastry, Shankar, http://robotics.eecs.berkeley.edu, Nov. 1, 1995, Total 8 pages.
Sastry, Shankar, "MilliRobotics in Minimally Invasive Telesurgery," Internet, http://robotics.eecs.berkeley.edu, 1996, 8 pages.
Supplementary European Search Report for Application No. EP00919930, mailed on May 9, 2003, 7 pages.
Supplementary Partial European Search Report for Application No. EP99966064, mailed on Jun. 12, 2007, 3 pages.
Taubes, Gary et al., "Surgery in Cyberspace," Discover magazine, Dec. 1994, vol. 15, issue 12, pp. 85-92.
Thring, M.W., Robots and Telechirs: Manipulators with Memory; Remote Manipulators; Machine Limbs for the Handicapped, 1983, pp. 9-11, 108-131, 194-195, 235-279; Ellis Horwood Limited, Chapter 5,7,8,9.
Trevelyan, James P. et al., "Motion Control for a Sheep Shearing Robot," IEEE Robotics Research Conference, the 1st International Symposium, Carroll, NH, USA., 1983, pp. 175-190, in Robotics Research, MIT Press.
Vibet, C., "Properties of Master Slave Robots," Motor-con, 1987, pp. 309-316.
Wei, Guo-Quing et al., "Real-Time Visual Servoing for Laparoscopic Surgery," IEEE Engineering in Medicine and Biology Magazine, Jan./Feb. 1997, pp. 40-45, vol. 16—Issue 1, IEEE.
Zhang, Xiaoli and Shahram Payandeh, "Application of Visual Tracking for Robotic-Assisted Laparoscopic Surgery," Journal of Robotic Systems, vol. 19, No. 7, pp. 315-328, 2002.

* cited by examiner fig.1 fig.2 fig. 3 fig. 4 fig. 5 fig. 6 fig. 7 fig.8 fig.9 ic # NON-FORCE REFLECTING METHOD FOR PROVIDING TOOL FORCE INFORMATION TO A USER OF A TELESURGICAL SYSTEM

CROSS REFERENCE TO RELATED APPLICATIONS

This application is a continuation-in-part of U.S. application Ser. No. 10/314,001 filed Dec. 5, 2002, now U.S. Pat. No. 7,107,090, which is a continuation of U.S. application Ser. No. 09/464,455 filed Dec. 14, 1999, now U.S. Pat. No. 6,522,906, which is a continuation-in-part of U.S. applicaion Ser. No. 09/457,406, filed Dec. 7, 1999, now U.S. Pat. No. 6,799,065, each of which is incorporated herein by reference.

This application is also a continuation-in-part of U.S. application Ser. No. 10/644,406, filed Aug. 19, 2003, now abandoned, which is a continuation of U.S. application Ser. No. 10/163,626, filed Jun. 5, 2002, now U.S. Pat. No. 6,671,581, which is a continuation of U.S. application Ser. No. 09/373,678, filed Aug. 13, 1999, now U.S. Pat. No. 6,424,885, which claims benefit of U.S. Provisional Applic. Ser. No. 60/128,160, filed Apr. 7, 1999, each of which is incorporated herein by reference.

FIELD OF THE INVENTION

The present invention generally relates to telesurgical systems and in particular, to a non-force reflecting method for providing tool force information to a user of a telesurgical system.

BACKGROUND OF THE INVENTION

Telesurgical systems are well-known and commonly used to robotically manipulate objects such as tools in remote or other environments where it is advantageous for a human not to do so in person. One example of such a system is the minimally invasive robotic surgery system described in commonly owned U.S. Pat. No. 6,699,177 entitled "Method and Apparatus for Performing Minimally Invasive Surgical Procedures," which is incorporated to the extent consistent herein by this reference.

To manipulate the remote object, a human operator or user of the telesurgical system manipulates or otherwise commands a locally provided master manipulator. Such commands to the master manipulator are then translated as appropriate, and sent to a remotely deployed slave manipulator. The slave manipulator then manipulates the object according to the user's commands.

In order to enhance the user's ability to "feel" the effects of his or her control inputs, force reflection is commonly included in telesurgical systems by having the remote slave manipulator feed back force or other motion relative signals to the master manipulator so that the user feels as if he or she is manipulating the controlled object directly by hand.

One problem with such force reflection telesurgical systems, however, is that a large feedback gain and/or signal filtering may cause the closed-loop control system between the master and slave manipulators to go unstable. Without such gain and/or filtering, however, the user may not properly feel objectionable force levels being applied by the manipulated object against obstructions in its path. In a minimally invasive surgical application such insensitivity to tool forces can result in the surgical tool exerting excessive forces so as to, for example, injure the patient or otherwise affect the safety or comfort of the patient in some manner.

OBJECTS AND SUMMARY OF THE INVENTION

Accordingly, one object of aspects of the present invention is a method for providing tool force information to a user of a telesurgical system without affecting the stability of the telesurgical system.

Another object of aspects of the invention is a method for providing tool force information to a user of a telesurgical system without restricting feedback gain or filter values and configurations while maintaining the stability of the telesurgical system.

Still another object of aspects of the invention is a method for providing tool force information to a user of a telesurgical system that effectively warns the user if excessive tool force is being applied against an obstruction in an environment in which the tool is being manipulated.

These and additional objects are accomplished by the various aspects of the present invention, wherein briefly stated, one aspect is a method for providing force information to a user of a telesurgical system, comprising: determining force values associated with a tool robotically manipulated in the telesurgical system; processing at least one of the force values to generate force information; and providing the force information to the user of the telesurgical system in a manner so as not to significantly affect the stability of the telesurgical system.

Another aspect is a method for providing force information to a user of a telesurgical system, comprising: determining force values associated with a slave manipulator for manipulating a tool; using one or more of the force values in a feedback path to a master manipulator operated by a user of the telesurgical system so that the master manipulator and the slave manipulator move substantially in tandem; processing at least one of the force values to generate force information; and providing the force information to the user in a manner so as to have substantially no effect on the stability of a closed-loop control system including the feedback path.

Still another aspect is a telesurgical system comprising: a slave manipulator having a plurality of joints for manipulating a tool; a master manipulator linked to the slave manipulator and operated by a user to control movement of the tool; a plurality of closed-loop control systems individually controlling movement of a corresponding one of the plurality of joints so that the slave manipulator manipulates the tool according to the operation of the master manipulator by the user; and a force indicator coupled to individual of the plurality of closed-loop control systems to provide force information generated from torque values for motors driving the plurality of joints in a manner to the user so as not to significantly affect the stability of the telesurgical system.

Additional objects, features and advantages of the various aspects of the present invention will become apparent from the following description of its preferred embodiment, which description should be taken in conjunction with the accompanying drawings.

DETAILED DESCRIPTION OF THE PREFERRED EMBODIMENT

Figure 1:
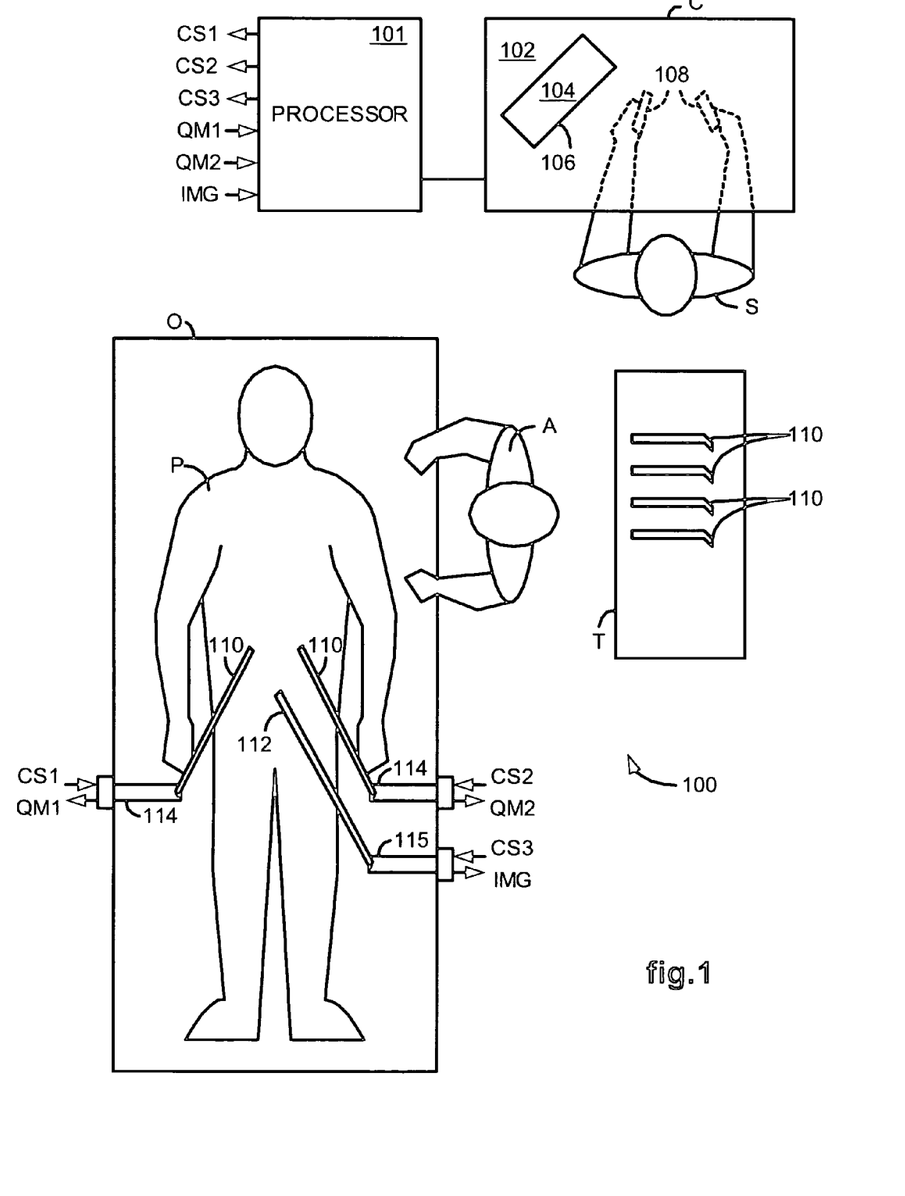
FIG. 1 illustrates a top view of an operating room employing a minimally invasive robotic telesurgical system utilizing aspects of the present invention.

FIG. 1 illustrates, as an example of a telesurgical system, a Minimally Invasive Robotic Surgical (MIRS) system 100 including a Console ("C") utilized by a Surgeon ("S") while performing a minimally invasive diagnostic or surgical procedure, usually with assistance from one or more Assistants ("A"), on a Patient ("P") who is lying down on an Operating table ("O").

The Console includes a support 102, a monitor 104 for displaying an image of a surgical site to the Surgeon, and one or more control devices 108 (also referred to herein cumulatively as a "master manipulator"). The control devices 108 may include any one or more of a variety of input devices such as joysticks, gloves, trigger-guns, hand-operated controllers, or the like.

The Surgeon performs a procedure by manipulating the control devices 108 which in turn, cause robotic mechanisms 114 (also referred to herein as "slave manipulators") to manipulate their respective removably coupled instrument or tool assembly 110 (hereinafter simply referred to as a "tool") through a minimally invasive incision in the body of the Patient while the Surgeon views the surgical site through the monitor 104.

To manipulate the tools 110, each of the slave manipulators 114 is conventionally formed of linkages that are coupled together and manipulated through motor controlled joints. Since the construction and operation of such robotic manipulators are well known, their details need not be repeated here. For example, general details on robotic manipulators of this type can be found in John J. Craig, *Introduction to Robotics Mechanics and Control,* $2^{nd}$ edition, Addison-Wesley Publishing Company, Inc., 1989.

The number of surgical tools 110 used at one time and consequently, the number of robotic mechanisms 114 in the system 100 will generally depend on the diagnostic or surgical procedure and the space constraints within the operating room among other factors. If it is necessary to change one or more of the tools 110 being used during a procedure, the Assistant may remove the tool 110 no longer being used at the time from its robotic mechanism 114, and replace it with another tool 110 from a tray ("T") in the operating room.

The Surgeon's Console is usually located in the same room as the Patient so that the Surgeon may directly monitor the procedure, is physically available if necessary, and is able to speak to the Assistant(s) directly rather than over the telephone or other communication medium. However, it will be understood that the Surgeon can also be located in a different room, a completely different building, or other remote location from the Patient allowing for remote surgical procedures.

Preferably, control devices 108 will be provided with the same degrees of freedom as their associated tools 110 to provide the Surgeon with telepresence, or the perception that the control devices 108 are integral with the tools 110 so that the Surgeon has a strong sense of directly controlling the tools 110. To this end, position, force, and tactile feedback sensors are preferably employed on the tools 110 to transmit position, force, and tactile sensations from the tools 110 back to the Surgeon's hands as he/she operates the control devices 108.

A monitor 104 is suitably coupled to a viewing scope assembly 112, including one or more cameras, through a processor 101, and positioned on the support 102 of the Console such that an image of the surgical site is provided near the Surgeon's hands. Preferably, the monitor 104 will display a projected image on a display 106 that is oriented so that the surgeon feels that he or she is actually looking directly down onto the operating site. To that end, an image of the tools 110 appear to be located substantially where the operator's hands are located even though the observation points (i.e., the endoscope or viewing camera) may not be from the point of view of the image.

In addition, the real-time image is preferably projected into a perspective image such that the operator can manipulate the end effector of a tool 110 through its corresponding control device 108 as if viewing the workspace in substantially true presence. By true presence, it is meant that the presentation of an image is a true perspective image simulating the viewpoint of an operator that is physically manipulating the tools 110. Thus, the processor 101 (or another processor in the Console) transforms the coordinates of the tools 110 to a perceived position so that the perspective image is the image that one would see if the viewing scope assembly 112 was located directly behind the tools 110.

The processor 101 performs various functions in the system 100. One important function that it performs is to translate and transfer the mechanical motion of control devices 108 to robotic mechanisms 114 through control signals such as CS1 and CS2 so that the Surgeon ("S") can effectively manipulate the tools 110. Another important function is to provide force information to one or more force indicators so that the Surgeon and/or Assistant(s) may be informed, for example, if excessive force is being applied by a monitored tool that may harm or cause discomfort to the Patient. In providing such force information, it is important that it is done in such a manner so as to not significantly affect the stability of the telesurgical system 100. In particular, it should not drive the telesurgical system 100 unstable.

The force indicators, for example, may be integrated or attached to the support 102, and/or displayed on the monitor 104. Force indicators may also be activated on the control devices 108 in the form of vibration or viscous feel as described herein, provided the control devices 108 are equipped for such tactile sensations. Force indicators may also be placed so as to be proximate to or positioned on their respective slave manipulators 114.

The force information, for example, may be derived from strain gauge measurements on linkages in the slave manipulator manipulating the tool that is being monitored, or it may be derived from encoders associated with joints in the slave manipulator manipulating the tool that is being monitored. Typical processing to generate the force information may include filtering and/or gain adjustments.

The processor 101 may be separate from or integrated as appropriate into the robotic mechanisms 114 and 115, it may be or be part of a stand-alone unit, or it may be integrated in whole or in part into the Console serving as its processor or as a co-processor to its processor. Although described as a processor, it is to be appreciated that the processor 101 may be implemented in practice by any combination of hardware, software and firmware. Also, its functions as described herein may be performed by one unit, or divided up among different components, each of which may be implemented in turn by any combination of hardware, software and firmware.

Figure 2:
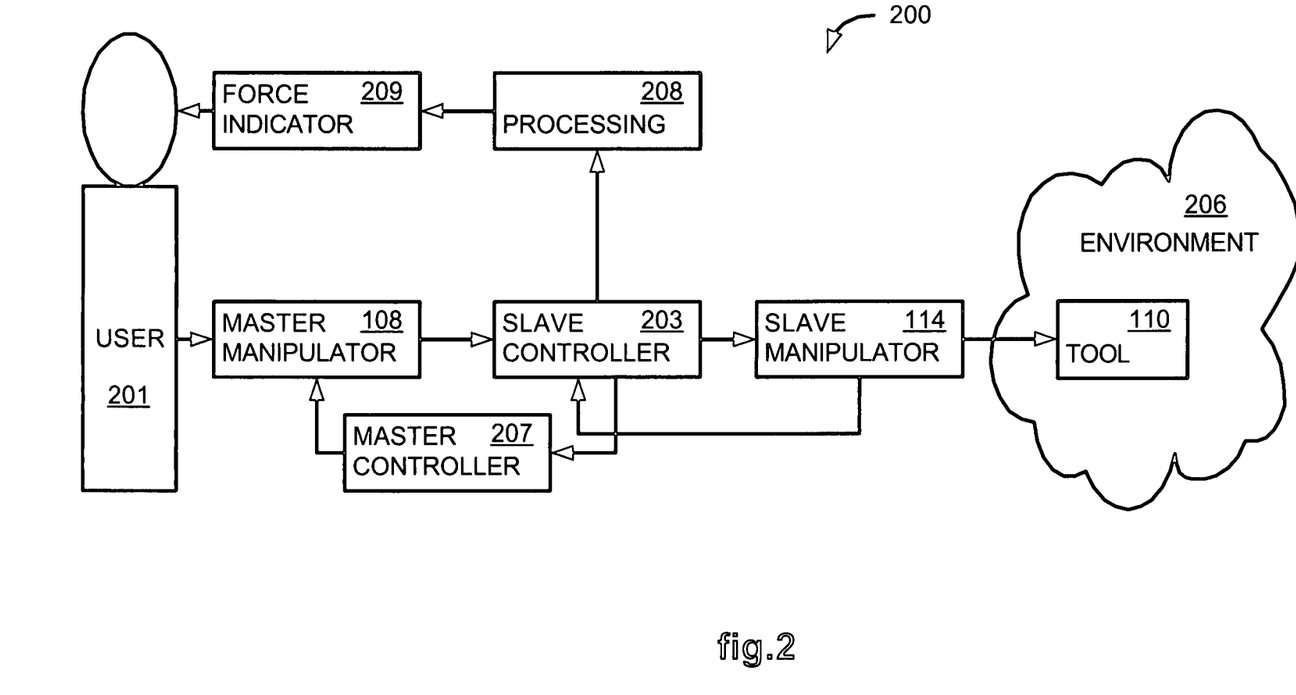
FIG. 2 illustrates a block diagram of a telesurgical system utilizing aspects of the present invention.

FIG. 2 illustrates, as an example, a block diagram of a telesurgical system 200 used in manipulating one of the tools 110 through its respective slave manipulator 114 in the MIRS system 100. The user 201 in this case is the Surgeon ("S") since it is the Surgeon ("S") who manipulates the master manipulator 108 in the MIRS system 100.

As the user 201 manipulates the master manipulator 108, the slave controller 203 translates its position from the coordinate frame of the master manipulator 108 to the coordinate frame of the tool 110. The slave controller 203 then determines the joint positions for the slave manipulator 114 that correspond to that tool position, and commands motors corresponding to each of those joints to move their respective joints to those positions using a closed-loop control system for each of the motors. Meanwhile, a master controller 207 feeds back any position error to the master manipulator 108 so that the master manipulator 108 tends to move in tandem along with the slave manipulator 114.

The functions of the slave controller 203 and the master controller 207 are implemented, for example, by programming them into a processor such as the processor 101 in the MIRS system 100. An example showing additional detail for such an implementation will now be described in reference to blocks 301-310 of FIG. 3. Referring to that figure, a closed-loop control system for driving a joint motor in the slave manipulator 114 is shown.

Figure 3:
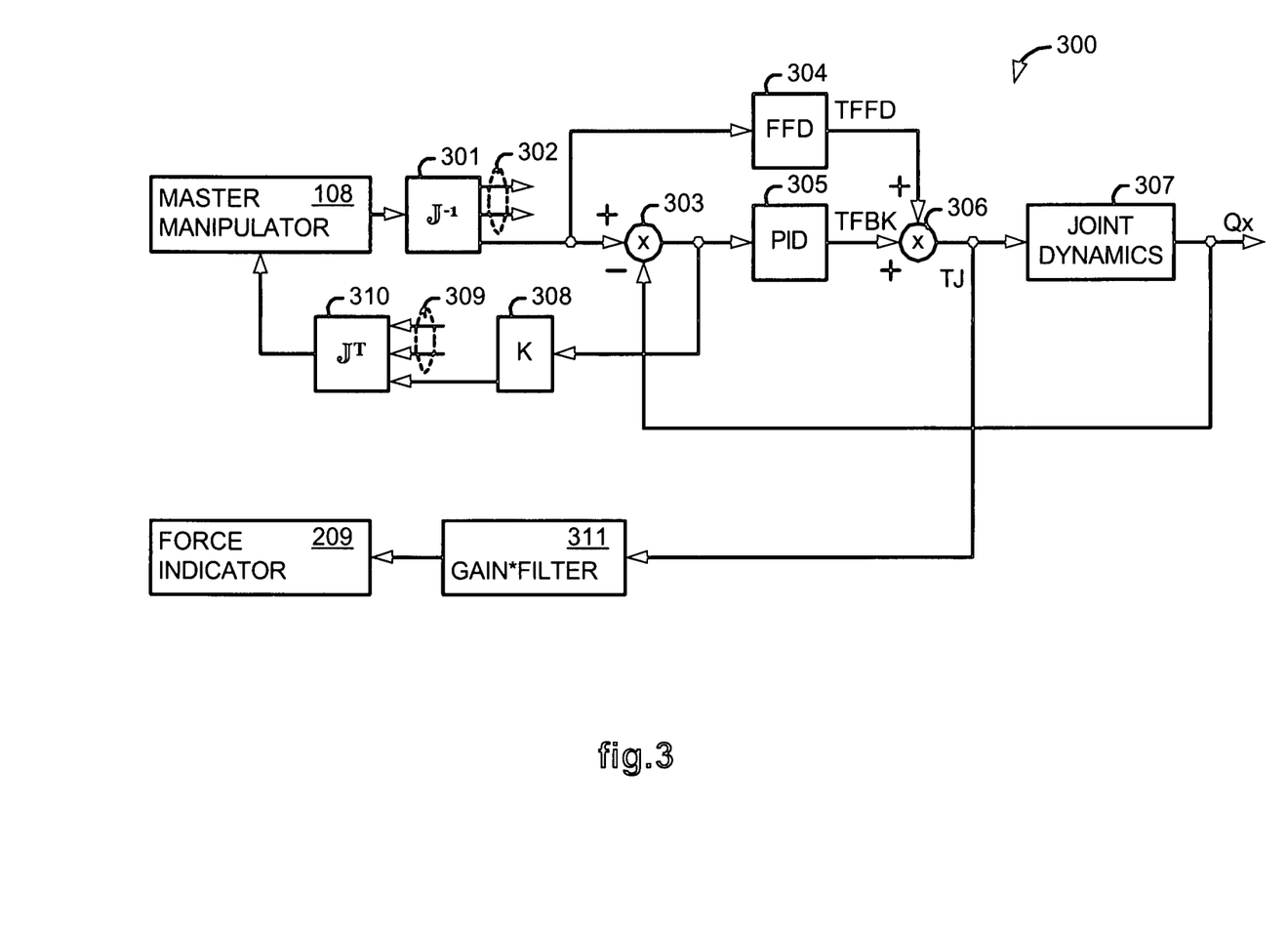
FIGS. 3-6 illustrate block diagrams of telesurgical systems using different joint torque values for tool force indication, utilizing aspects of the present invention.

In this example, the closed-loop control includes a proportional, integral, derivative ("PID") function 305 and a feed-forward ("FFD") gain 304. Although a PID function is described herein, it is to be appreciated, however, that different control laws may also be implemented and are fully contemplated to be within the full scope of the various aspects of the present invention. As indicated by the sets of arrows 302 and 309, the master manipulator 108 is understood to also be driving other similarly configured closed-loop control systems corresponding to other joints of the slave manipulator 114.

The PID function 305 generates a feedback torque command ("TFBK") by operating on the joint position error between a commanded joint position from the inverse Jacobian 301 (ignoring coordinate transformations) and the detected joint position "Qx" from the joint encoder. The FFD gain 304 generates a feed-forward torque command ("TFFD") by operating on the commanded joint position, velocity, and acceleration. The feedback torque (TFBK) and the feed-forward torque ("TFFD") are then added together to generate a total torque command ("TJ") that is applied to the joint motor, whose dynamics are depicted along with those of its joint in block 307, which is labeled JOINT DYNAMICS.

The joint position error is also provided to the master manipulator 108 through a gain ("K") 308 and transpose Jacobian 310. Although not shown to simplify the example, it is to be appreciated that a coordinate transformation from slave joint space to Cartesian space is also generally performed at this point. Since forces applied to the tool 110 such as a static force experienced when the tool 110 is pressing against an obstruction can create a joint position error, such reflected forces are effectively passed back to the master manipulator 108 by such position error being fed back.

One problem with the part of the telesurgical system described so far with respect to FIG. 2 is that additional filtering and/or gain to increase the sensitivity for detecting certain forces on the tool is difficult, since those changes may drive the joint closed-loop control systems incorporated therein to unstable conditions. As an example, if a relatively low level force is applied for an extended period of time by the tool against an obstruction such as the Patient's rib-cage, it may not be detected through the reflected forces being provided through the position error that is fed back to the master manipulator 108 due to a low value of the gain "K" 308 that is required to maintain system stability. As a consequence, bruising and/or prolonged discomfiture by the Patient during and/or after the minimally invasive surgical procedure may result.

Accordingly, referring back to FIG. 2 now, a force indicator 209 and processing unit 208 are added to the telesurgical system 200 to provide such types of tool force information to the user 201 without affecting the stability of the closed-loop control systems in the telesurgical system 200. In this case, the processing function 208 processes force or torque information received from the slave controller 203 substantially without restriction as to gain or filtering, because it is outside of the closed-loop control systems previously described herein. As an example of such processing, the generation of force information to be provided to the force indicator 209 may comprise: generating a Cartesian force by multiplying the torque values by an inverse transform of the Jacobian matrix, generating a filtered force by filtering the Cartesian force with a low pass filter to remove unwanted high frequency noise, generating a filtered scalar force by taking a norm of the filtered force, and generating a static force by multiplying the filtered scalar force by a velocity dependent multiplier that is relatively small at high velocities and large at low velocities, wherein the velocity dependent multiplier is a natural exponential function with power of $-Av$, where v is a column vector of joint velocities and A is a tunable row matrix used to tune and weight the joint velocities as desired.

Figure 4:
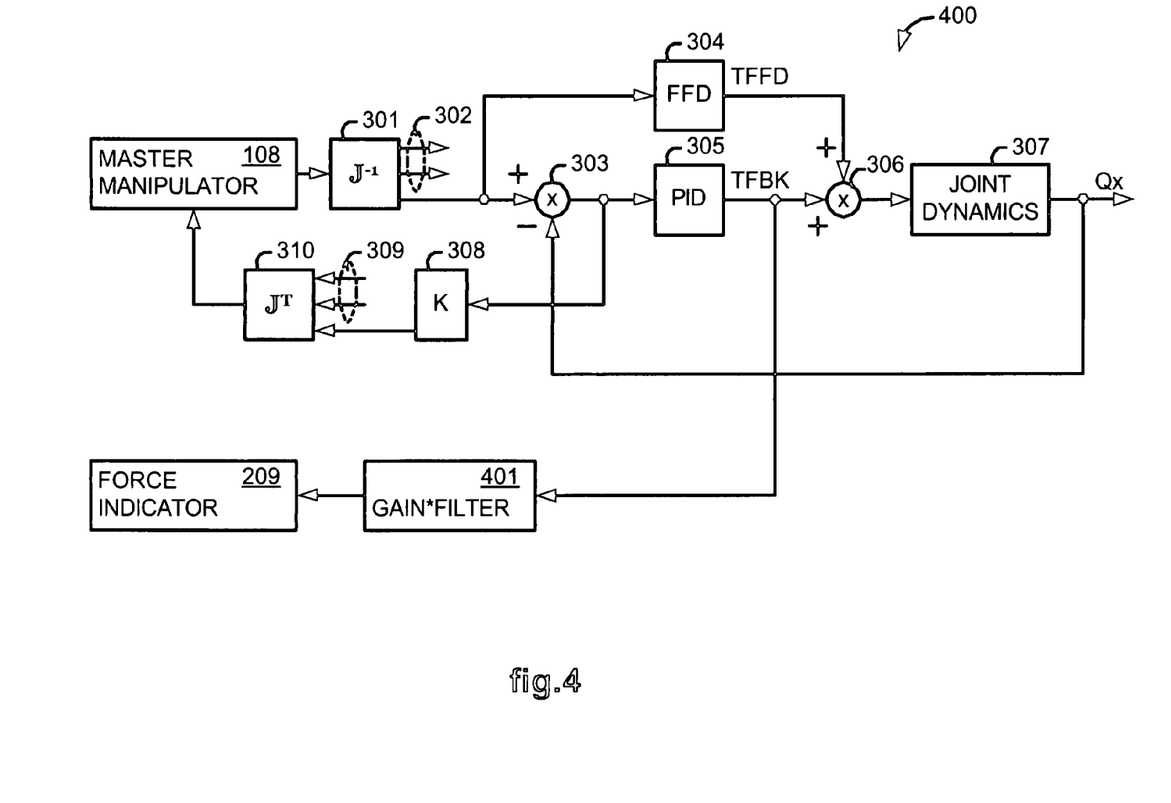
Figure 5:
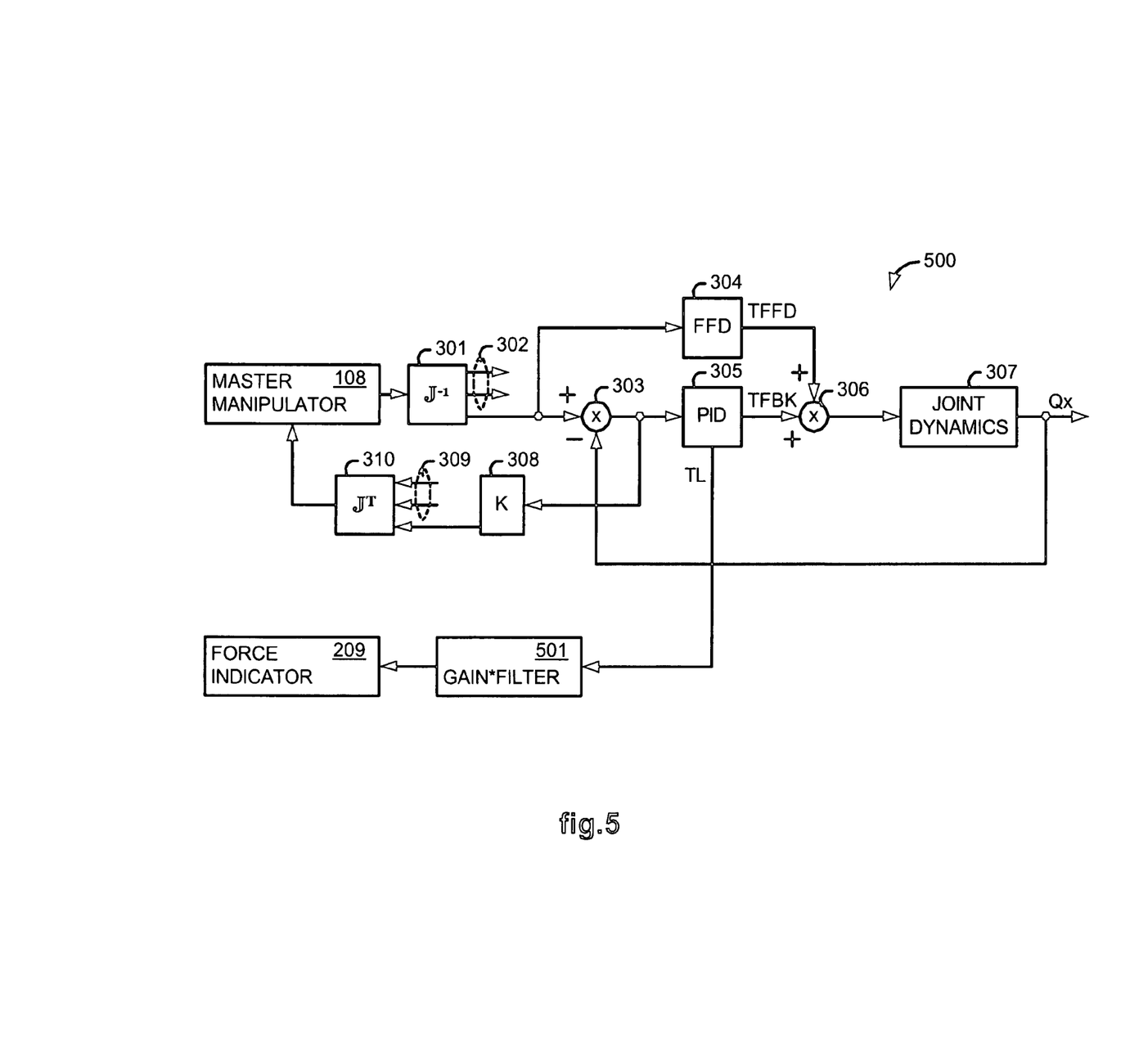
Figure 6:
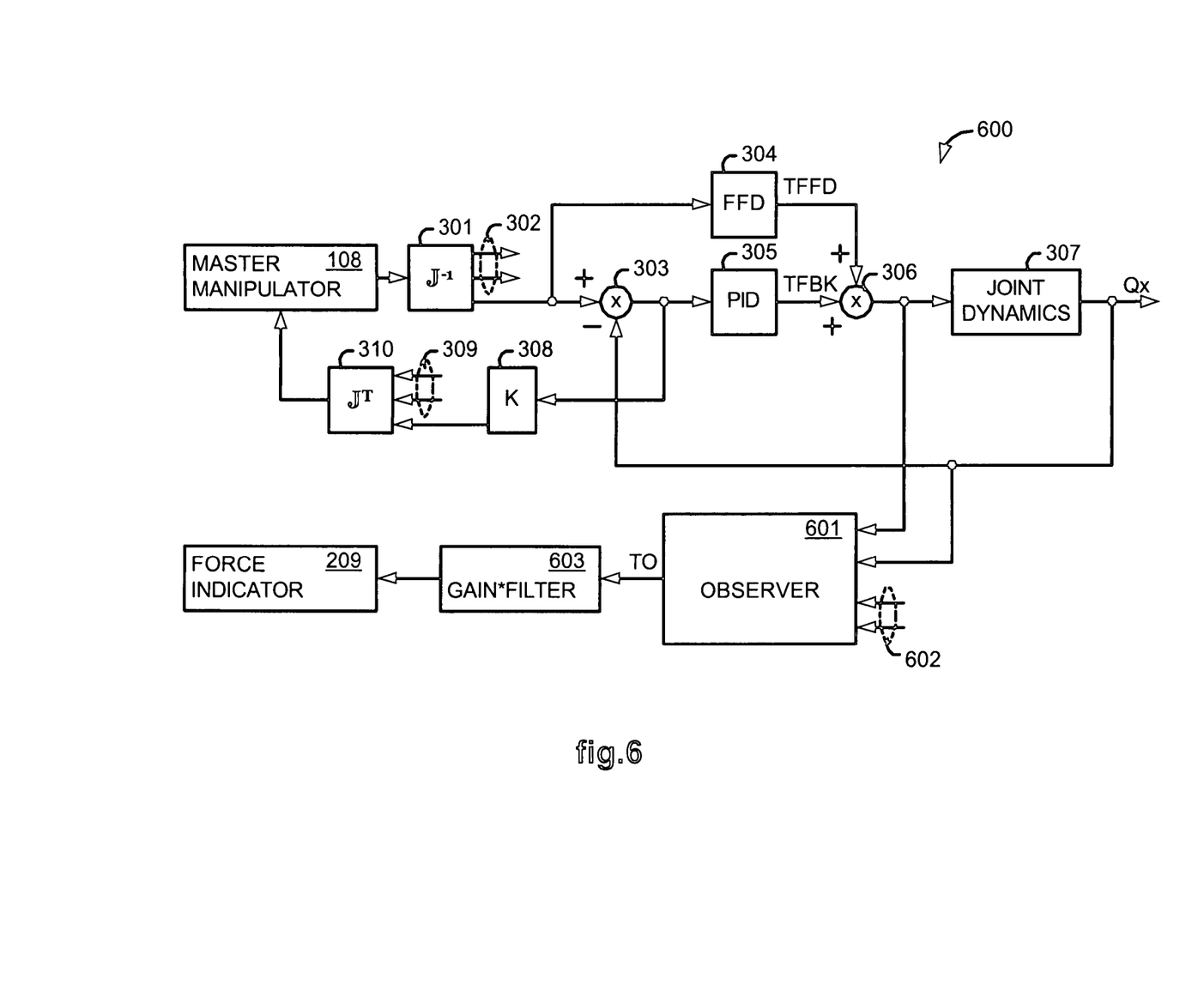
Figure 7:
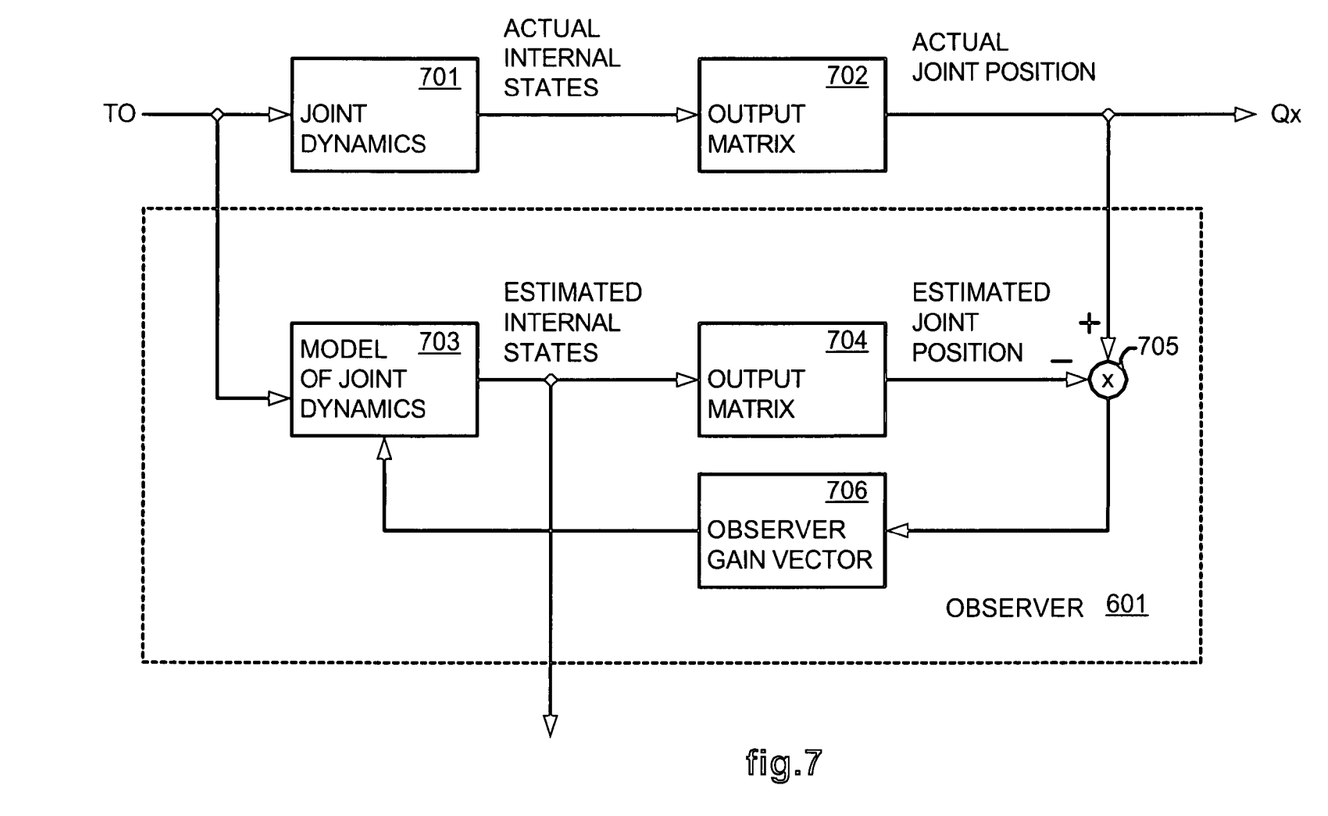
FIG. 7 illustrates a block diagram of an observer useful in the telesurgical system of FIG. 6.

As shown in FIGS. 3-6, the force or torque information from the slave controller 203 may be picked-off from several different points in the joint motor control systems. For example, in FIG. 3, the total joint torque ("TJ") command provided to the joint motor may be picked-off for generating the force information to be provided to the user 201 through the force indicator 209. In FIG. 4, the feedback torque ("TFBK") generated by the PID function 305 is picked-off for generating the force information. In FIG. 5, the integrator torque ("TL") from the integrator in the PID function 305 is picked-off for generating the force information. In FIG. 6, an observed disturbance torque "TO" that is generated by an observer 601 is used for generating the force information to be provided to the user 201 through the force indicator 209. An example of the observer 601 is illustrated FIG. 7. Since observers of this type are well-known in robotic control theory, detailed discussion of this figure is deemed unnecessary.

Note that depending upon the force that is to be presented to the user 201, the picked-off force locations may differ for different joints of the slave manipulator 114, and only selected ones of the joints may be tapped for picking off force or torque information. In addition, the gains and filters used for processing the picked-off force or torque values may be different for each of the joints. The processed force information thus picked off the joint control systems for the selected joints are then combined in an appropriate fashion before providing the force information to the user 201 through the force indicator 209.

The force indicator 209 may take any one of many different forms or modalities that is preferably turned-on or activated and turned-off or deactivated according to force threshold criteria. In the following examples, the force information is generated so as to determine a static force produced as the tool is pressed against an obstruction.

In one example of the force indicator 209, the force information may be provided to the user by turning on a user-visible indicator when information of the static force is greater than a first threshold value, and turning off the user-visible indicator when the information of the static force is less than a second threshold value. In this case, the first threshold value would generally be greater than the second threshold value.

One example of the user-visible indicator is a bar graph which may be displayed on the screen 106 of the monitor 104 of the MIRS system 100 so that it is visible to the user of the telesurgical system. In this case, as the static force asserted against the tool increases, the length of the bar graph increases accordingly.

Another example of the user-visible indicator is a blinking icon on the screen 106 of the monitor 104. Similarly, the user-visible indicator may be a flashing light on the support 102 of the Console or on the master manipulator 108 of the MIRS system 100 where the Surgeon would be able to readily see it, or the flashing light may be on or in the proximity of the slave manipulator 114 of the MIRS system 100 where the Surgeon and/or the Assistant(s) may be able to see it.

The color of the user-visible indicator may also change as the static force increases, such as going from green (indicating a safe level of force), to yellow (indicating a warning that the force is getting close to an unsafe or undesirable level), and to red (indicating an unsafe or undesirable level of force has been reached). In addition or alternatively to a change in color, the intensity of the user-visible indicator may change as the static force changes.

Another type of force indicator 209 is a user-audible indicator which preferably increases in intensity as the magnitude of the applied force increases. Another type of force indicator 209 uses haptic or tactile sensation features that may be implemented on the master manipulator 108, such as a haptic "buzz" that provides a buzzing sensation to the Surgeon while manipulating the master manipulator 108 or a haptic "viscosity" that makes operation of the master manipulator 108 feel more sluggish to the Surgeon. In the case of these tactile sensations being activated on the master manipulator 108, the frequency and/or amplitude of the "buzz" or the "viscosity" should be limited so as not to substantially affect the stability of the closed-loop control systems of the telesurgical system.

Figure 8:
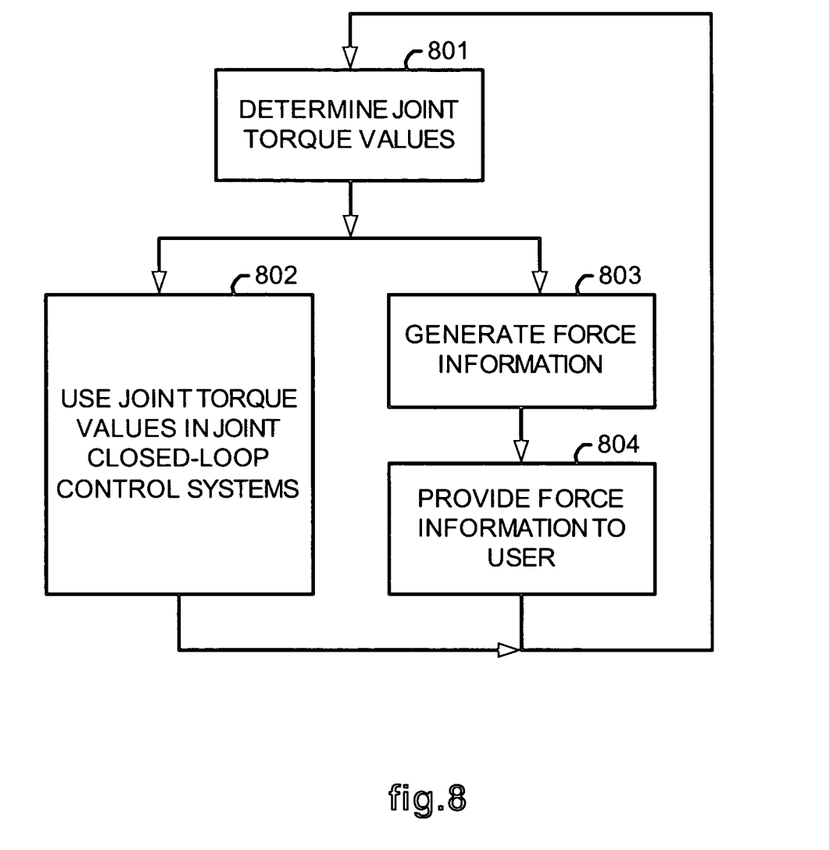
FIG. 8 illustrates a flow diagram of a method for providing force information to a user of a telesurgical system utilizing aspects of the present invention.

FIG. 8 illustrates a method for providing force information to the user 201 which is implemented, for example, by the addition of the force indicator 209 and the processing unit 208 to the telesurgical system 200. In 801, torque values are determined for joints employed in the telesurgical system for manipulating a tool. The torque values in this case are determined, for example, by the slave controller 203 processing the movement of the master manipulator 108 as manipulated by the user 201 (to determine TFFD, for example) and the movement of the joints of the slave manipulator 114 (to determine TFBK, for example).

The operation of the closed-loop controls systems and the providing of force information to the user may then take place concurrently. In particular, in 802, the determined joint torque values are used in their respective closed-loop control systems, for example, as described in reference to blocks 301-310 of FIG. 3, while in 803, at least one of the torque values is processed to generate force information for the tool, and in 804, the force information is provided to the user of the telesurgical system in a manner so as not to significantly affect the stability of the joint closed-loop control systems.

Figure 9:
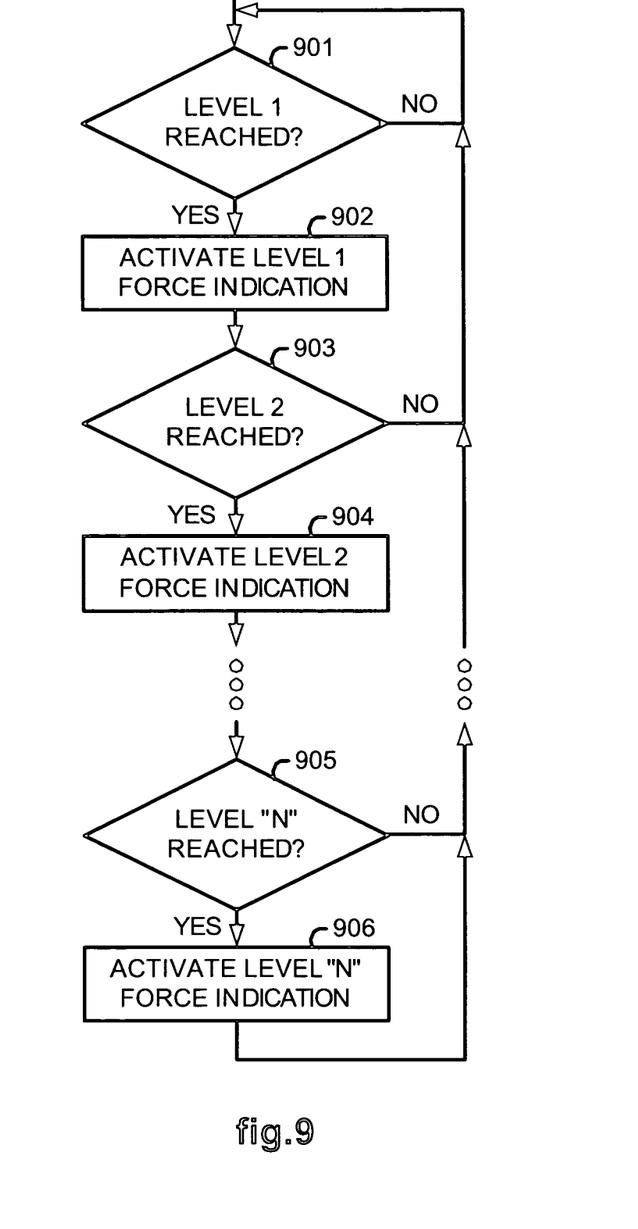
FIG. 9 illustrates a flow diagram of a method for providing force information to a user of a telesurgical system with escalating warnings, utilizing aspects of the present invention.

Although the processing function 208 of the telesurgical system 200 is shown as being a simple gain and/or filter in corresponding blocks of FIGS. 3-6, it is to be appreciated that the processing may take on additional sophistication such as illustrated in FIG. 9. In particular, as shown in that figure, various force indications may be activated as the static force asserted on the tool increases. At each level, the force indication may be a different color or intensity as described previously herein, or it may be a different modality. For example, the level 1 force indication may be a user-visible indication, the level 2 force indication may be a user-audible indication, and the level 3 force indication may be a tactile sensation on the master manipulator 108. As in the cases of the slave controller 203 and the master controller 207, the processing function 208 is also implemented in a processor such as the processor 101 in the MIRS system 100.

Although the various aspects of the present invention have been described with respect to a preferred embodiment, it will be understood that the invention is entitled to full protection within the full scope of the appended claims.

We claim:

1. A method for providing force information to a user of a telesurgical system, wherein the telesurgical system includes a tool, a slave manipulator having a plurality of joints for manipulating the tool, a master manipulator, and a first closed-loop control system for driving a first joint of the plurality of joints in response to manipulation of the master manipulator by a user, the method comprising:
   processing at least a first value at a first node in the first closed-loop control system to generate force information indicative of a force being exerted against the tool, wherein the processing includes at least one of multiplying the first value by a first gain and passing the first value through a first filter, wherein the force being exerted against the tool results in a reflected force being applied to the master manipulator through at least the first closed-loop control system; and
   providing the force information to the user of the telesurgical system in a non-tactile sensory manner so as to be detectable by the user, wherein the providing is initiated upon the force being exerted against the tool being greater than a first threshold value, and wherein the first threshold value corresponds to a reflected force that is less than a minimum force level which is tactilely detectable on the master manipulator by the user.

2. The method according to claim 1, wherein the force information is provided to the user so as to warn the user if excessive force is being applied by the tool against an obstruction.

3. The method according to claim 1, wherein the force information is provided to the user by displaying the force information on a user-visible indicator.

4. The method according to claim 3, wherein the providing of the force information to the user is terminated upon the force being exerted against the tool being less than a second threshold value which is less than the first threshold value.

5. The method according to claim 3, wherein the user-visible indicator increases in intensity as the magnitude of the applied force increases.

6. The method according to claim 3, wherein the user-visible indicator is in the form of a bar graph.

7. The method according to claim 3, wherein the telesurgical system includes a monitor having a screen visible to the user, and the user-visible indicator is a blinking icon displayed on the screen.

8. The method according to claim 3, wherein the user-visible indicator is located in the proximity of the slave manipulator.

9. The method according to claim 8, wherein the user-visible indicator is a flashing light.

10. The method according to claim 1, wherein the force information is provided to the user by using a user-audible indicator.

11. The method according to claim 10, wherein the user-audible indicator increases in intensity as the magnitude of the applied force increases.

12. The method according to claim 1, wherein the force information is provided to the user in the non-tactile sensory manner by turning on a first indicator upon the force being exerted against the tool being greater than the first threshold value, and wherein the force information is provided to the user in the non-tactile sensory manner by turning on a second indicator upon the force being exerted against the tool being greater than a third threshold value which is greater than the first threshold value.

13. The method according to claim 1, wherein the first value at the first node derives from an encoder measurement taken at the first joint.

14. The method according to claim 13, wherein the generation of the force information comprises generating a Cartesian force by using an inverse transform of a Jacobian matrix corresponding to the slave manipulator.

15. The method according to claim 14, wherein the generation of the force information further comprises generating a filtered force by filtering the Cartesian force with a low pass filter to remove unwanted high frequency noise.

16. The method according to claim 15, wherein the generation of the force information further includes generating a filtered scalar force by taking the norm of the filtered force.

17. The method according to claim 16, wherein the generation of the force information further includes generating a static force by multiplying the filtered scalar force by a velocity dependent multiplier that is relatively small at high velocities and large at low velocities.

18. The method according to claim 17, wherein the velocity dependent multiplier is a natural exponential function with power of $-Av$, where v is a column vector of joint velocities and A is a tunable row matrix used to tune and weight the joint velocities as desired.

19. The method of claim 1, wherein the telesurgical system includes a second closed-loop control system for driving a second joint of the plurality of joints in response to manipulation of the master manipulator by the user, wherein the generation of the force information includes at least processing a second value at a second node in the second closed-loop control system, and wherein the processing includes at least one of multiplying the second value by a second gain and passing the second value through a second filter.

20. The method of claim 19, wherein the first and second closed-loop control systems are similarly configured, and wherein the first and second nodes correspond to different locations in the first and second closed-loop control systems.

21. The method of claim 19, wherein the first and second gains are different values.

22. The method of claim 19, wherein the first and second filters process input values differently.

* * * * *